United States Patent
Boudin et al.

(10) Patent No.: US 10,241,036 B2
(45) Date of Patent: Mar. 26, 2019

(54) LASER THERMOGRAPHY

(71) Applicant: SIEMENS ENERGY, INC., Orlando, FL (US)

(72) Inventors: Dustin C. Boudin, Belmont, NC (US); Anand A. Kulkarni, Charlotte, NC (US)

(73) Assignee: SIEMENS ENERGY, INC., Orlando, FL (US)

( * ) Notice: Subject to any disclaimer, the term of this patent is extended or adjusted under 35 U.S.C. 154(b) by 0 days.

(21) Appl. No.: 15/588,853

(22) Filed: May 8, 2017

(65) Prior Publication Data
US 2018/0321140 A1    Nov. 8, 2018

(51) Int. Cl.
| | |
|---|---|
| *G01N 21/35* | (2014.01) |
| *G01M 15/14* | (2006.01) |
| *G01J 5/00* | (2006.01) |
| *G01J 5/08* | (2006.01) |
| *G01N 21/88* | (2006.01) |
| *G01N 25/72* | (2006.01) |

(52) U.S. Cl.
CPC ............ *G01N 21/35* (2013.01); *G01J 5/0088* (2013.01); *G01J 5/0896* (2013.01); *G01M 15/14* (2013.01); *G01N 21/8851* (2013.01); *G01N 25/72* (2013.01); *G01N 2201/06113* (2013.01)

(58) Field of Classification Search
CPC ............ G01J 2005/0077; G01J 5/0088; G01J 5/0896; G01N 21/39; G01N 21/35; G01N 25/20; G01N 25/72; G01N 21/954; G01N 2021/399; G01N 21/359; G01N 2291/02881; G01N 21/9515; G01N 21/8851; G01N 2201/06113; G01M 15/14

USPC ......................................................... 250/340
See application file for complete search history.

(56) References Cited

U.S. PATENT DOCUMENTS

| | | | | |
|---|---|---|---|---|
| 5,111,048 A | * | 5/1992 | Devitt | G01N 25/72 |
| | | | | 250/341.6 |
| 5,383,024 A | * | 1/1995 | Maxey | G01J 3/4412 |
| | | | | 356/28.5 |
| 5,823,474 A | * | 10/1998 | Nunnally | B64F 5/27 |
| | | | | 244/134 E |
| 5,963,292 A | * | 10/1999 | Rivir | G01F 1/7044 |
| | | | | 349/199 |
| 6,206,325 B1 | * | 3/2001 | Nunnally | B64D 15/00 |
| | | | | 244/134 E |

(Continued)

FOREIGN PATENT DOCUMENTS

DE          10338582 A1    3/2005

OTHER PUBLICATIONS

PCT International Search Report and Written Opinion of International Searching Authority dated Jul. 9, 2018 corresponding to PCT International Application No. PCT/US2018/025819 filed Apr. 3, 2018.

*Primary Examiner* — Taeho Jo

(57) ABSTRACT

A non-destructive method for condition assessment of a turbine component is provided. The method includes providing a laser generating a light pulse that heats the turbine component. An infrared image is then captured of the heated turbine component. An analysis of the turbine component for a particular characteristic of the turbine component may then be done. A system for the non-destructive condition assessment of a turbine component is also provided.

12 Claims, 2 Drawing Sheets

(56) References Cited

U.S. PATENT DOCUMENTS

| | | | | |
|---|---|---|---|---|
| 6,469,794 B1* | 10/2002 | Piltch | G01N 21/6408 | 356/601 |
| 6,653,971 B1* | 11/2003 | Guice | A01M 1/026 | 342/22 |
| H002197 H * | 8/2007 | Gord | 250/343 | |
| 7,420,662 B2* | 9/2008 | Yalin | F02D 35/022 | 356/317 |
| 7,535,565 B1* | 5/2009 | Viertl | G01N 21/718 | 356/318 |
| 7,722,793 B2* | 5/2010 | Gueguen | B23K 26/34 | 264/447 |
| 8,107,086 B2* | 1/2012 | Hart | A61C 5/90 | 356/601 |
| 8,544,279 B2* | 10/2013 | Sappey | F01D 21/003 | 431/75 |
| 8,920,023 B2* | 12/2014 | Sloan | G01N 25/04 | 374/102 |
| 9,797,709 B2* | 10/2017 | Inard-Charvin | G01B 21/085 | |
| 2002/0027941 A1 | 3/2002 | Schlagheck et al. | | |
| 2002/0158202 A1* | 10/2002 | Webber | F23N 5/003 | 250/339.13 |
| 2003/0055594 A1* | 3/2003 | Bunker | G01K 11/30 | 702/134 |
| 2004/0191064 A1* | 9/2004 | Guo | B23P 6/007 | 416/191 |
| 2004/0262521 A1* | 12/2004 | Devitt | G01N 25/72 | 250/341.1 |
| 2006/0032471 A1* | 2/2006 | Yalin | F02P 23/04 | 123/143 B |
| 2007/0217672 A1* | 9/2007 | Shannon | G06T 7/0006 | 382/152 |
| 2008/0095714 A1* | 4/2008 | Castella | A61B 5/0066 | 424/9.3 |
| 2008/0291465 A1* | 11/2008 | Lorraine | G01N 21/1717 | 356/502 |
| 2009/0079110 A1* | 3/2009 | Gueguen | B23K 26/34 | 264/482 |
| 2009/0245321 A1* | 10/2009 | Ringermacher | G01N 25/72 | 374/5 |
| 2010/0027014 A1* | 2/2010 | Hart | A61C 5/90 | 356/436 |
| 2010/0067756 A1* | 3/2010 | Hart | A61C 5/90 | 382/128 |
| 2010/0296083 A1* | 11/2010 | Patel | G01J 5/0003 | 356/237.3 |
| 2011/0043820 A1* | 2/2011 | Sansom | G01B 11/0616 | 356/503 |
| 2011/0180521 A1* | 7/2011 | Quitter | B23K 26/03 | 219/121.73 |
| 2011/0189379 A1* | 8/2011 | Ortner | G01N 25/72 | 427/9 |
| 2011/0253690 A1* | 10/2011 | Dane | G02B 27/0927 | 219/121.74 |
| 2012/0045330 A1* | 2/2012 | Wu | F03D 7/042 | 416/1 |
| 2012/0121382 A1* | 5/2012 | Xu | F01D 25/002 | 415/118 |
| 2012/0140234 A1* | 6/2012 | Masterson | F02C 7/00 | 356/445 |
| 2012/0154813 A1* | 6/2012 | Li | G01N 21/3504 | 356/437 |
| 2012/0201489 A1* | 8/2012 | Zheng | G01B 11/14 | 385/12 |
| 2013/0003152 A1* | 1/2013 | Belousov | G01B 11/162 | 359/9 |
| 2013/0027516 A1* | 1/2013 | Hart | A61B 1/00082 | 348/45 |
| 2013/0114088 A1* | 5/2013 | Newman | G01B 9/02 | 356/520 |
| 2013/0148689 A1* | 6/2013 | Yahaba | G01N 25/72 | 374/5 |
| 2014/0033799 A1* | 2/2014 | Newman | G01B 9/02 | 73/37 |
| 2014/0176965 A1* | 6/2014 | Hart | A61C 5/90 | 356/630 |
| 2015/0092814 A1 | 4/2015 | Wolfgruber | | |
| 2015/0168352 A1* | 6/2015 | Sohn | F03D 17/00 | 73/643 |
| 2015/0260667 A1* | 9/2015 | Isakov | G01N 25/72 | 374/5 |
| 2015/0298166 A1* | 10/2015 | Poullos | B05D 3/06 | 427/8 |
| 2016/0097719 A1* | 4/2016 | Cheverton | G01J 5/10 | 250/459.1 |
| 2016/0201181 A1* | 7/2016 | Tuppen | F01D 5/286 | 148/510 |
| 2017/0011503 A1* | 1/2017 | Newman | G01N 25/72 | |
| 2017/0046831 A1* | 2/2017 | Inagaki | G01N 25/72 | |
| 2017/0052070 A1* | 2/2017 | Marsh | H04N 5/332 | |
| 2017/0070686 A1* | 3/2017 | Boudin | H04N 5/33 | |

* cited by examiner

LASER THERMOGRAPHY

BACKGROUND

1. Field

The present disclosure relates generally to a method and system for non-destructive inspection of components, and more particularly, to a method and system for non-destructive inspection of turbine components using laser thermography.

2. Description of the Related Art

In many industrial applications, non-destructive testing methods are used to evaluate components without causing damage. One such application of non-destructive testing uses flash thermography to test components of a turbine engine such as a turbine blades or vanes, combustor baskets, or a transition component. These components frequently consist of a substrate coated with a thermal barrier coating that protects the substrate from high temperatures and a corrosive environment. For example, coated gas turbine components may require testing to determine the thickness of the thermal barrier coating or whether the coating has any cracking or delaminations, sections where the coated layer has become separated from the substrate. A severe crack or delaminated layer may cause component failure during normal operation of the turbine.

Currently, inspection and testing of coated turbine components may be done using flash thermography, a commonly used non-destructive testing method in which the surface of the component is heated by a light pulse typically lasting only a few milliseconds. Under normal conditions, the part cools after flash heating, as the heat deposited at the surface flows toward the cooler interior. However, internal anomalies in the test piece, such as voids, inclusions, delamination, moisture, or changes in thickness or density, cause changes in the cooling rate at the surface. An infra-red camera is then used to capture infra-red radiation emitted by the component to form a thermographic image. The internal anomalies as referenced above would be visible in the thermographic image.

While flash thermography enables non-destructive testing of components, there are some disadvantages using flash lamps as a light/heat source. For example, the flash lamps are bulky and produce light/heat over a larger area of the component than what may be of interest for a testing sample. The heat generated decays over time and produces a significant amount of background noise such that one must use filters to attenuate the signal in order to filter out this background noise. Additionally, flash lamps require a significant amount of time to heat up the component to a desired temperature. In contrast, a laser will come to a desired temperature quickly. Also, it is easier to obtain information using flash thermography regarding the surface layer, or thermal barrier coating of a turbine component, than the subsurface layer. Obtaining information regarding the subsurface layer is possible using flash thermography, however, a lot of data is captured during the inspection requiring a significant amount of time to analyze the captured data.

Consequently, a non-destructive inspection method that will overcome these disadvantages is desired.

SUMMARY

Briefly described, aspects of the present disclosure relates to a non-destructive method and system for the condition assessment of a turbine component.

A non-destructive method for condition assessment of a turbine component is provided. The method includes providing a laser generating a light pulse that heats the turbine component. An infrared image is then captured of the heated turbine component. One can then analyze the turbine component for a particular characteristic of the turbine component.

A system for non-destructive condition assessment of a turbine component is provided. The system includes a laser source which generates a light pulse that heats a turbine component. An infrared camera including an infrared sensor for detecting thermal energy radiated by the turbine component is used to capture at least one image of the turbine component. The radiated thermal energy is transmitted to the infrared sensor to enable the generation of the infrared image.

DETAILED DESCRIPTION

To facilitate an understanding of embodiments, principles, and features of the present disclosure, they are explained hereinafter with reference to implementation in illustrative embodiments. Embodiments of the present disclosure, however, are not limited to use in the described systems or methods.

The components and materials described hereinafter as making up the various embodiments are intended to be illustrative and not restrictive. Many suitable components and materials that would perform the same or a similar function as the materials described herein are intended to be embraced within the scope of embodiments of the present disclosure.

Lasers can provide intense energy using short pulses, mainly due to the on/off switch. This significantly reduces the background intensity that is achieved with conventional flash sources like flash lamps. Thus, lasers may be used to heat the surface of materials very rapidly. Additionally, the beam of the laser is highly controllable having a very localized focus area. A method of using a laser as the heating source for thermographic non-destructive testing of coated gas turbine components is thus presented.

Multiple laser wavelengths are available enabling one to view surface characteristics of a component as well as the subsurface characteristics using the same testing setup. Because an overlay layer, also referred to as a surface layer, such as a thermal barrier coating of a coated component is transparent to certain wavelengths, the test sample information may be tailored so that at these wavelengths a subsurface temperature rise may be induced in the component. This temperature signal for the subsurface layer may be digitally recorded with infrared imaging, or active thermography.

Figure 1:
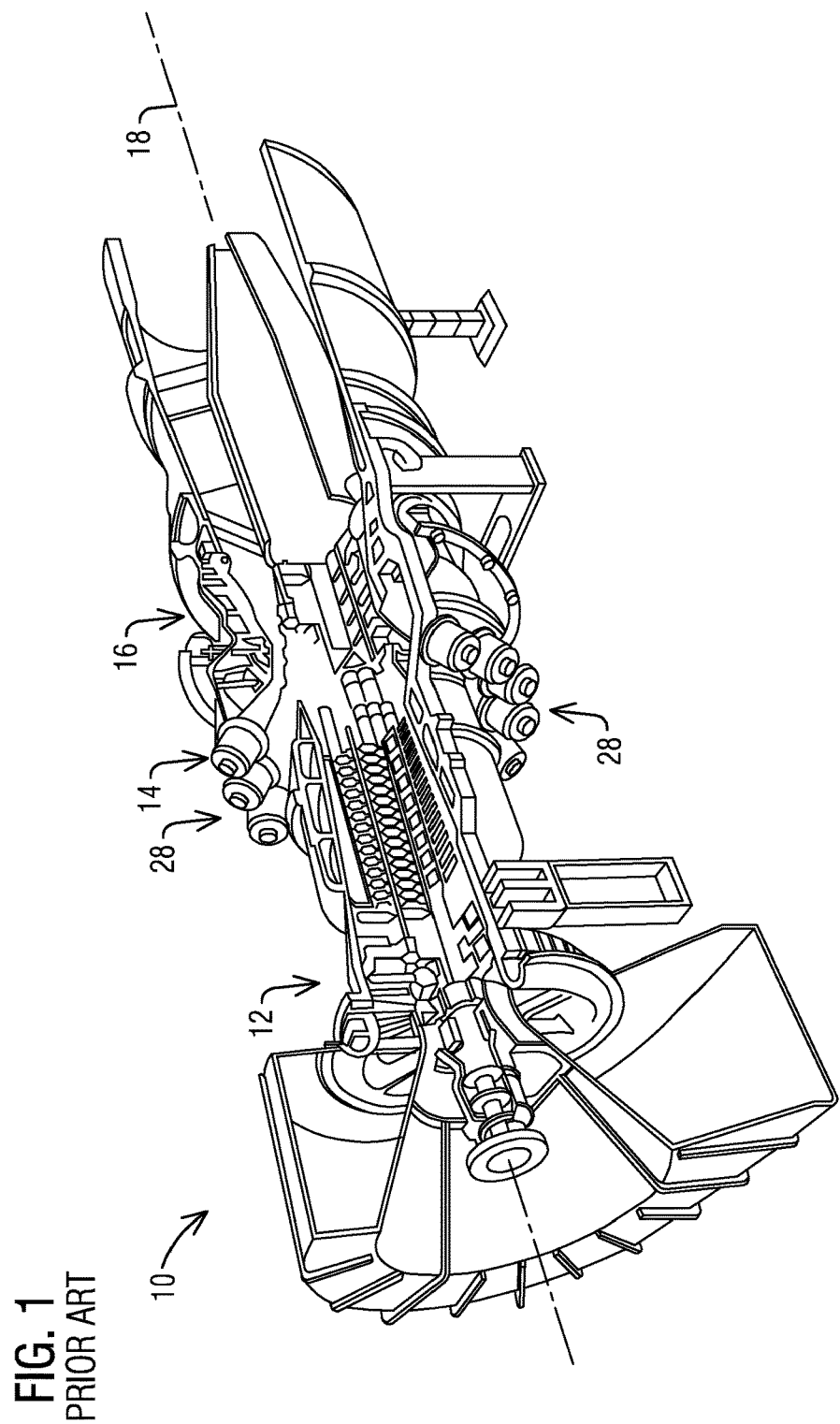
FIG. 1 illustrates a side partial cross sectional view of an axial flow gas turbine.

Referring to FIG. 1, an industrial gas turbine engine 10 is shown. The engine 10 includes a compressor section 12, a combustor section 14, and a turbine section 16 arranged along a horizontal center axis 18. The combustor section 14 includes a plurality of combustors 28. A hot working gas is conveyed from the combustor section 14 through to the turbine section 16.

Sections of the turbine 10 that are exposed to the hot gases as the gases travel along a hot gas path in the turbine 10 may include a ceramic-based coating that serves to minimize exposure of the base metal of a component, such as an airfoil base metal, to high temperatures that may lead to oxidation of the base metal. Such a coating may be a known thermal barrier coating (TBC) that is applied onto a bond coating formed on the base metal.

A turbine 10 is typically operated for extended periods. The TBC layer or both the TBC and bond coat layers may undesirably deteriorate or delaminate during operation of the turbine 10. This exposes the base metal to high temperatures, which may lead to oxidation of the base metal. The turbine 10 is inspected at periodic intervals to check for wear damage and other undesirable conditions that may have occurred with respect to various internal components. In addition, the TBC and bond coat layers are routinely inspected to determine the degree of deterioration of the TBC and bond coat layers (i.e., remaining thickness of the layers) and other undesirable conditions when the turbine engine is shut down or prior to assembly.

Figure 2:
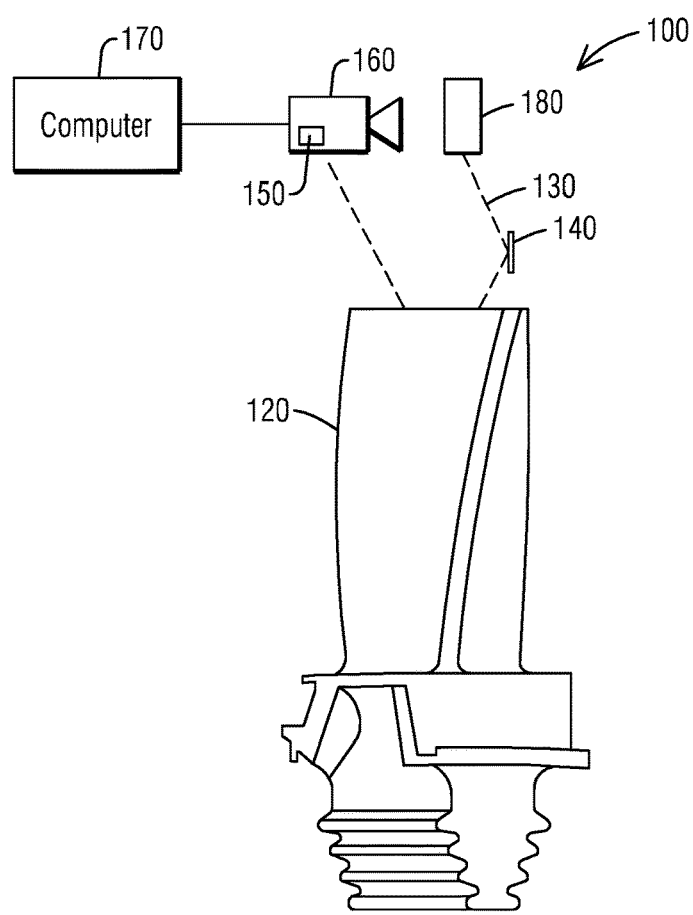
FIG. 2 illustrates a laser thermography system for imaging a turbine component.

Referring now to FIG. 2, a system for the non-destructive 100 condition assessment of a turbine component 120 in accordance with an embodiment is shown. A laser source 180 generates a light pulse 130 that heats up the turbine component 120. The system includes an infrared (IR) camera 160 having an infrared sensor 150 for detecting thermal energy in the infrared region of the electromagnetic spectrum. The detected thermal energy is radiated by the turbine component 120 and transmitted to the infrared sensor 150. The IR camera 160 is configured to capture IR images of a turbine component 120. A mirror 140 may be used to focus the light pulse 130 from the laser source 180 onto the turbine component 120. In the illustrated embodiment, a turbine blade is shown as the turbine component 120, however, one skilled in the art would understand that other turbine components may be used as well. The IR sensor 150 is communicatively coupled to a computer 170 by an electrical connection or a wireless connection.

The computer 170 may include a central processing unit, a memory, and an input/output interface. The computer is generally coupled through the I/O interface to a display for visualization and various input devices that enable user interaction with the computer 170 such as a keyboard. For example, from the I/O interface a user may load the component 120 into the computer 170 by identifying the type of component to be inspected. Using the identified type of component, the computer 170 may automatically position the cameras 160 according to pre-programmed positions stored in memory in order to capture a desired image.

Figure 3:
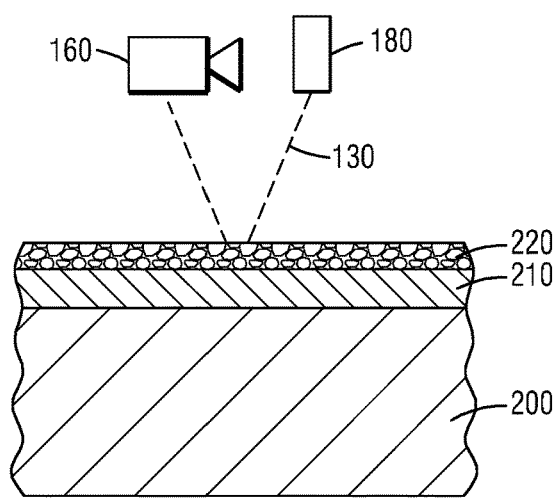
FIG. 3 illustrates a coated turbine component assessed non-destructively using laser thermography.

As discussed previously, a turbine component 120, in particular a turbine blade or vane, may comprise a base layer, also called the substrate, overlaid with a bond coating to which a TBC is applied. FIG. 3 illustrates a cross section of such a coated turbine component 120. A substrate 200 is overlaid with a bond coating 210 to which a thermal barrier coating 220, TBC, is applied. The substrate 200 may comprise a superalloy material.

Referring to FIGS. 1-3, a non-destructive method for the condition assessment of a turbine component is also provided. A laser source 180 may be provided which generates a light pulse 130 that heats up a turbine component 120. An infrared image may be captured of a desired portion of the turbine component 120. A characteristic of the turbine component 120 on infrared image may then be analyzed. FIG. 3 illustrates an embodiment of a light pulse generated from a light source being focused onto a coated turbine component. An IR camera captures the IR radiation emitted from the coated turbine component and captures the data in the form of an IR image.

In order to capture data concerning the thermal barrier coating 220 on the surface of the turbine component 120 as well as data concerning the subsurface which may include the substrate 200 and/or the bond coat 210, the method may be used by changing the wavelength of the laser source 180. For example, the laser source 180 may be activated at a first specified wavelength in order to capture data regarding the thermal barrier coating 220. The laser source 180 would then be focused to flash a desired area of a surface of the turbine component 120 for a first pulse duration. An IR camera 160 may be used to capture a desired area of the surface of the turbine component 120. The laser source 180 may then be deactivated at the first specified wavelength. Next, in order to obtain data regarding the subsurface, which may include the bond coat 210 and/or the substrate 200, the laser source 180 may be activated at a second specified wavelength. The bond coat 210 and the substrate 200 typically have similar characteristics such that they heat up similarly. The laser source 180 would then be focused to flash the desired area of a surface of the turbine component 120 for a second pulse duration. The IR camera 160 may be used to capture the desired area of the subsurface of the turbine component 120. The laser source 180 may then be deactivated at the second specified wavelength.

The laser source 180 may be a laser flash lamp which provides duration pulses of broadband light of varied wavelengths and high radiant intensities. A laser source 180 may emit wavelengths between 4-9 microns, considered midwave, and 9-15 microns being considered long wave. The surface, or thermal barrier coating, is opaque at wavelengths between 4-9 microns such that the TBC characteristics may be captured in a thermal image in this range. However, the material characteristics of the thermal barrier coating make the TBC transparent to a laser wavelength of approximately 9-11 microns. Thus, at the laser wavelengths in the range of 9-11 microns, the subsurface or bond coat 210 and/or substrate 200, data may be captured in a thermal image. In an embodiment, the wavelength of the laser may be set to 9.5-10.5 microns. The duration of the light pulse 130 depends on the turbine characteristic to be analysed, however, the light pulse 130 duration may lie in the range of 1-30 ms. For a specified area, the first pulse duration and the second pulse duration may be the same in the case of uniform ceramic and metal thickness or different in the case of large differences in the layer thicknesses.

The acquired data may be analyzed in order to assess the condition of the turbine component 120. The analysing may be accomplished by running algorithms on the computer 170 in order to process the acquired pixelated data. The analysis may include examining the heat decay in the desired area over time and may transform the time space information into depth information. Assessing the condition of the turbine component 120 may include comparing acquired data of the desired area with known parameters to determine defects on the component such as delaminations. Defects or discontinuities will show up in a thermographic image as a different temperature change than normal surface or subsurface conditions. Also, one may assess the condition of the turbine component 120 by measuring the thickness of a thermal barrier coating 220 on the substrate 200 of the turbine component 120. In an embodiment, the thickness of the thermal barrier coating 220 on the component 120 at different inspection intervals may be tracked during the component's lifetime.

Advantages of laser thermography compared to flash thermography include: better temperature control of the light source and a shorter time period for the laser to heat up, reducing the amount of time needed to inspect the component. Also, using a laser provides the flexibility to change the wavelength with the result that the substrate may be more easily inspected simply by switching the wavelength of the laser. So, both inspections, inspection of the thermal barrier coating as well as the substrate, may be done at one time in the same test setup. It may be appreciated that the data gathered on the turbine component may be stored and referenced for future use, such as for example, statistical analysis on the turbine component. The statistical data may be used by the computer to track the health of the turbine component over time.

While embodiments of the present disclosure have been disclosed in exemplary forms, it will be apparent to those skilled in the art that many modifications, additions, and deletions can be made therein without departing from the spirit and scope of the invention and its equivalents, as set forth in the following claims.

What is claimed is:

1. A non-destructive method for condition assessment of a turbine component, comprising:
    providing a laser generating a light pulse that heats the turbine component;
    capturing at least one infrared image of the heated turbine component;
    analyzing a turbine component characteristic on the at least one image; and
    activating the laser at a first specified wavelength;
    focusing the laser to flash heat a desired area of a surface of the turbine component for a first pulse duration; and
    capturing an infrared image of the desired area of the surface of the turbine component;
    deactivating the laser at the specified wavelength;
    activating the laser at a second specified wavelength;
    focusing the laser to flash heat the desired area of a subsurface of the turbine component for a second pulse duration; and
    capturing a second infrared image of the desired area of the subsurface of the turbine component,
    wherein the first image contains a first set of data regarding the desired area of the surface of the turbine component and the second image contains a second set of data regarding the desired area of the subsurface the turbine component, and
    wherein the first specified wavelength and the second specified wavelength are different, and
    wherein the specified wavelength only flash heats the surface and the second specified wavelength only flash heats the subsurface of the component,
    wherein the analyzing includes comparing the first set of data with known material parameters in order to assess the surface for damage,
    wherein the analyzing includes comparing the second set of data with known material parameters in order to assess the subsurface for damage, and
    wherein the pulse duration of the laser is in a range of 1-30 ms.

2. The method as claimed in claim 1, wherein the first specified wavelength is in a range of 4-9 microns.

3. The method as claimed in claim 1, wherein the second specified wavelength is in a range of 9-11 microns.

4. The method as claimed in claim 3, wherein the second specified wavelength is in a range of 9.5-10.5 microns.

5. The method as claimed in claim 1,
    wherein the capturing is performed by an infrared camera including an infrared sensor for detecting thermal energy radiated by the turbine component, and
    wherein the radiated thermal energy is transmitted to the infrared sensor to enable generation of the infrared image.

6. The method as claimed in claim 1, wherein the surface of the turbine component includes a thermal barrier coating and the subsurface of the turbine component includes a bond coating and/or a substrate.

7. The method as claimed in claim 1, wherein the laser is a laser flash lamp.

8. The method as claimed in claim 1, wherein the focusing of the laser is accomplished using a mirror.

9. A system for non-destructive condition assessment of a turbine component, comprising:
    a laser source, wherein the laser source generates a light pulse that flash heats the turbine component;
    an infrared camera including an infrared sensor for detecting thermal energy radiated by the turbine component wherein the radiated thermal energy is transmitted to the infrared sensor to enable generation of the infrared image; and
    a turbine component,
    wherein the infrared camera captures at least one infrared image of the turbine component,
    wherein the turbine component comprises a thermal barrier coating and/or a bond coating overlying a substrate,
    wherein the laser source is configured to flash heat an area of a surface of the turbine component for a time duration at a first specified wavelength in order to capture a first infrared image of the thermal barrier coating,
    wherein the laser source is configured to flash heat the area of a subsurface of the turbine component for a pulse duration at a second specified wavelength in order to capture a second infrared image of the bond coat and/or substrate,
    wherein the first specified wavelength only flash heats the surface and the second specified wavelength only flash heats the subsurface of the component, and
    wherein the pulse duration of the laser is in a range of 1-30 ms.

10. The system as claimed in claim 9, further comprising a mirror which focuses the light pulse onto the turbine component.

11. The system as claimed in claim 9, wherein the first specified wavelength is in a range of 4-9 microns.

12. The system as claimed in claim 9, wherein the second specified wavelength is in a range of 9-11 microns.

* * * * *